(12) United States Patent
Mays et al.

(10) Patent No.: US 6,225,812 B1
(45) Date of Patent: May 1, 2001

(54) METHOD AND APPARATUS FOR MEASURING THE DENSITY OF A SUBSTANCE HAVING FREE WATER COMPENSATION

(75) Inventors: David L. Mays, Woodstock, GA (US); Ira B. Goldberg; Charles S. Hollingsworth, both of Thousand Oaks, CA (US)

(73) Assignee: Rockwell Technologies, LLC, Thousand Oaks, CA (US)

( * ) Notice: Subject to any disclaimer, the term of this patent is extended or adjusted under 35 U.S.C. 154(b) by 0 days.

(21) Appl. No.: 09/104,661

(22) Filed: Jun. 25, 1998

(51) Int. Cl.⁷ .................................................. G01N 22/04
(52) U.S. Cl. ............................................ 324/634; 324/636
(58) Field of Search ................................. 324/636, 634, 324/643, 640; 131/299, 295

(56) References Cited

U.S. PATENT DOCUMENTS

| | | | |
|---|---|---|---|
| 3,458,808 | * 7/1969 | Agdur | 324/636 |
| 4,257,001 | * 3/1981 | Partain | 324/636 |
| 5,397,993 | * 3/1995 | Tews | 324/636 |
| 5,648,038 | * 7/1997 | Fathi | 324/636 |

* cited by examiner

*Primary Examiner*—Safet Metjahic
*Assistant Examiner*—Jose M. Solis
(74) *Attorney, Agent, or Firm*—William R. Walbrun; John J. Horn

(57) ABSTRACT

A method and apparatus for measuring the amount of free water contained within a substance includes a waveguide having front and back sides disposed opposite each other. The waveguide defines a chamber for propagating a microwave signal therethrough. The waveguide has an end perpendicular to the front and back sides which forms a short within the chamber. The front and back sides each have an aperture for passing a substance therethrough. A microwave signal in the frequency range of 10–25 gigahertz is directed through the chamber wherein the generated microwave signal is reflected back from the short of the end. The generated and reflected signals form a ratio which is used by a microprocessor along with the measurement from an adjacent sensor that provides a dielectric constant measurement corresponding to the density of the substance in order to determine a weight of the substance compensated for free water.

21 Claims, 3 Drawing Sheets

METHOD AND APPARATUS FOR MEASURING THE DENSITY OF A SUBSTANCE HAVING FREE WATER COMPENSATION

BACKGROUND OF THE INVENTION

1. Field of the Invention

The present invention relates generally to measurement techniques. More particularly, the invention pertains to measurement techniques for determining the density of a substance having free water compensation. It has particular relation to the manufacturing of tobacco cigarettes where measurement techniques are employed in a continuous manufacturing process.

2. Description of the Prior Art

In the manufacturing industry, the need exists for determining the density of a substance as it is being processed on a real-time basis. Modern cigarette manufacturing machines, for example, produce a continuous paper and tobacco rod, which is cut into individual cigarettes by downstream apparatus. The density of the tobacco in the rod must be continuously measured, with the measurements directed back to the manufacturing machine for use in the control process of the machine.

Using radio frequency energy to measure the dielectric constant of small segments of the substance, such as the cigarette rod, and by knowing the physical properties of the cigarette rod's constituents, density profiles and weights can be calculated. An apparatus employing the above technique is disclosed in U.S. Pat. No. 5,698,986 issued to Mays et al.

The apparatus measures how the substance affects the resonance frequency of a microwave cavity. The resonance frequency of a microwave cavity depends on the size of the cavity and on the dielectric constant of the substance contained in the cavity. If the substance is a gas borne powder or mass of particles, the resonance frequency will be different from the resonance frequency determined when only the gas is present. This will in turn indicate the density of the powder, or the relative proportions of two powders if a mixture is introduced into the cavity, or any number of other desired measurements.

One source of error in this measurement technique is related to varying amounts of free water which may be contained within the substance. Accordingly, the need exists, in those applications where a substance may contain free water, to measure the free water content and to compensate the weight measurement.

Various methods for water measurement are also known in the art. One common method includes a source of microwave energy that is propagated through a particular substance and is attenuated by an amount dependent on the quality of moisture in the product. For example, U.S. Pat. No. 5,086,279 issued to Wochnowski et al. discloses a method and apparatus for measuring the moisture content of fibrous material in accordance with the previously described technique. U.S. Pat. No. 3,535,629 issued to Gibson et al. discloses another microwave moisture measuring apparatus. While systems such as those described above have provided some degree of success in measuring moisture, there still remains a need for improved systems. For example, in both systems described above, microwave energy is not contained within the system and is radiated outwardly which allows for potential interference with other RF systems, such as radio communication services. Still other known systems are not adapted for use in a continuous production system or are not designed or readily adapted for use with a cigarette manufacturing machine. Accordingly, the needs exists for a free water measuring device that can operate on a production line on a real-time basis with the density monitor of Mays et al.

As will be described in greater detail hereinafter, the method and apparatus of the present invention solves the aforementioned problems and employs a number of novel features that render it highly advantageous over the prior art.

SUMMARY OF THE INVENTION

Accordingly, it is an object of this invention to provide a method and apparatus for determining the free water within a substance.

Another object of this invention is to provide a method and apparatus for providing free water compensation for use in combination with a density sensor, as well as providing temperature compensation.

Another object of this invention is to provide an apparatus that contains RF energy to prevent the same from radiating outside of the apparatus.

Still another object of this invention is to provide an apparatus that is usable in a manufacturing process having a continuously moving material.

Yet another object of this invention is to provide an apparatus that can be used with a cigarette manufacturing machine.

To achieve the foregoing and other objectives, and in accordance with the purposes of the present invention an apparatus is provided for measuring the free water contained within a substance. The apparatus includes a waveguide having front and back sides disposed opposite each other. The waveguide defines a chamber for propagating a microwave signal therethrough. The waveguide has an end perpendicular to the front and back sides which forms a short within the chamber. The front and back sides each have an aperture extending substantially perpendicular therethrough for receiving a substance to be measured. The waveguide has a connector aperture in communication with the chamber and is adapted for receiving a microwave signal source. The microwave signal source generates a microwave signal in the frequency range of 10–25 gigahertz (GHz) through the chamber wherein the generated microwave signal is reflected back from the short of the end.

In accordance with an aspect of the invention, a coupler is connected to the microwave signal source to transmit the microwave signal into and out of the connector aperture. An amplifier is provided to amplify and convert to voltage signals, both the microwave signal generated through the chamber and reflected back from the short. A divider receives the voltage signals and generates a corresponding ratio which is converted into a digitized signal by an analog-to-digital converter.

A microprocessor receives the digitized signal along with a dielectric constant measurement from a density sensor. Using these measurements along with previously knowing the properties of the constituents within the substance to be measured, the processor determines the weight of substance and compensates for the amount of free water represented by the ratio.

In the manufacture of tobacco cigarettes, a tobacco rod is formed by forming a sheet of tobacco paper into a tube and inserting particles of tobacco into the tube as it is formed. The tobacco rod is directed in a continuous production fashion through the aperture of the waveguide and an aperture of the density sensor positioned adjacent thereto. As the processor calculates the weight of a portion of the rod extending through the apertures, the processor generates a control signal corresponding to the weight calculation. This control signal can be utilized in the control process of forming the tobacco rod by adding more or fewer particles of tobacco to the rod in response to the control signals so that a desired weight range for a section of rod can be maintained throughout the process.

Other objects, features and advantages of the invention will become more readily apparent upon reference to the following description when taken in conjunction with the accompanying drawings, which drawings illustrate several embodiments of the invention.

DETAILED DESCRIPTION OF THE PREFERRED EMBODIMENT

Figure 1:
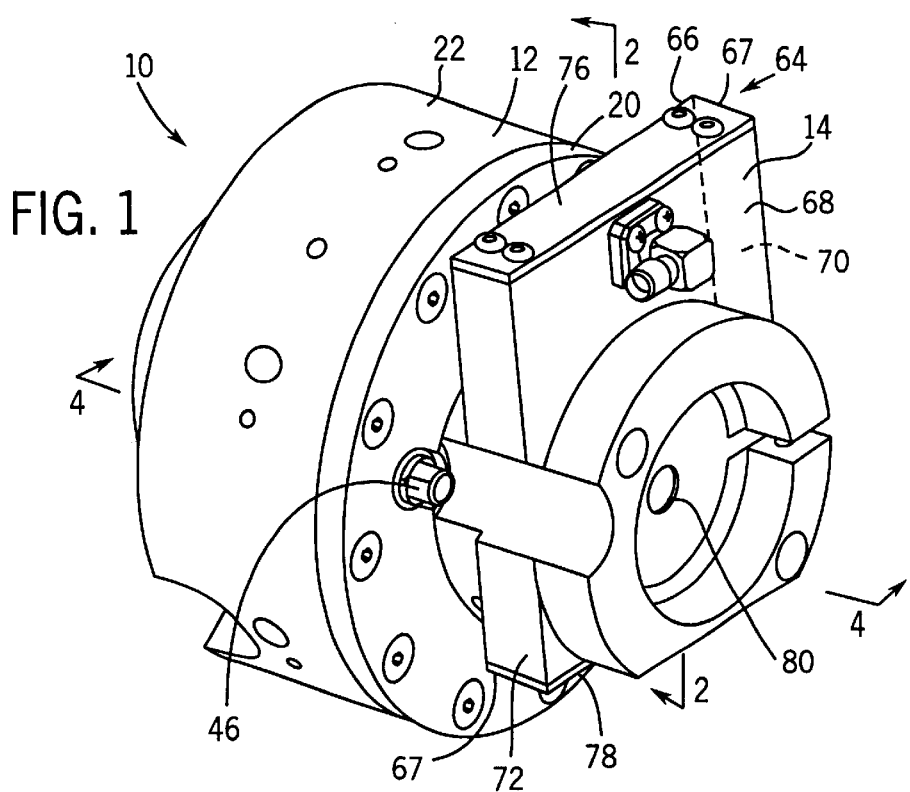
FIG. 1 is a perspective view of the present invention.

Referring now to the drawings, an improved cigarette density monitor 10 of the present invention is illustrated in FIG. 1. The density monitor 10 includes a density sensor 12 and a free water sensor 14 which provides compensation measurements for amounts of free water contained in a substance.

In the following description, numerous specific details are set forth in order to provide a thorough understanding of the present invention. It will be obvious, however, to one skilled in the art that the present invention may be practiced without these specific details. In other instances, well-known circuits, structure and techniques have not been shown in detail in order not to unnecessarily obscure the present invention.

Figure 4:
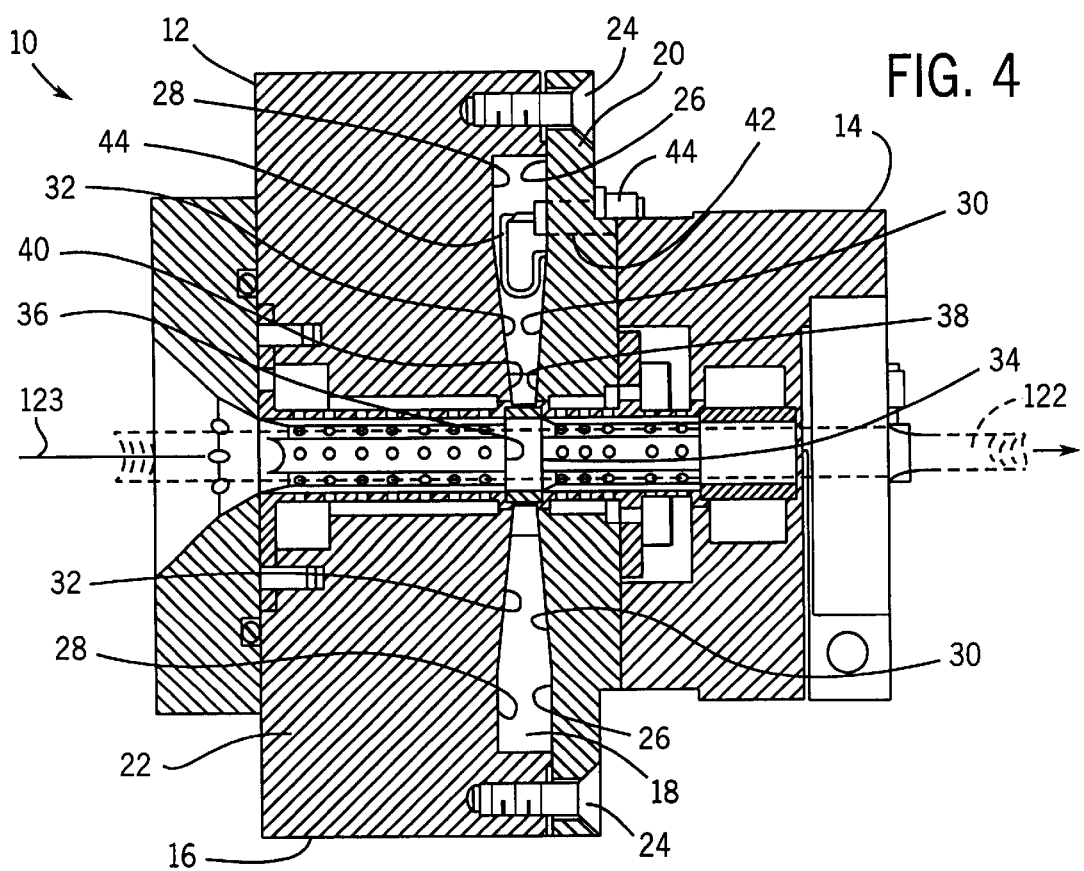
FIG. 4 is a section view taken along line 4—4 of FIG. 1.

Referring to FIG. 4, the density sensor 12 includes an essentially cylindrical container 16 surrounding a resonant cavity 18. The resonant cavity 18 is defined by a first member 20 and second member 22 secured together by bolts 24. The first and second members 20, 22 each define a conductive annular surface 26, 28, a conductive frusto-conical surface 30, 32, and one of a first aperture 34, 36.

The conductive annular surface 26 is disposed coaxially with and parallel to the conductive annular surface 28, at a surface separation distance therebetween. An interior edge 38 of the frusto-conical surface 30 and an interior edge 40 of the frusto-conical surface 32 are disposed opposite each other and have separation distance from each other which is less than the surface separation distance described above.

The first member 20 also includes a third aperture 42 which allows microwaves to be injected into, or reflected out of the cavity 18. The third aperture 42 is sized to receive an antenna 44 or other suitable coupling or impedance matching device. The antenna 44 may be a loop, as shown. If desired, it may instead be a probe, namely, a metal rod from the center conductor of a coaxial cable attached to the first member 20 with a coupler 46, as illustrated in FIG. 1.

Figure 5:
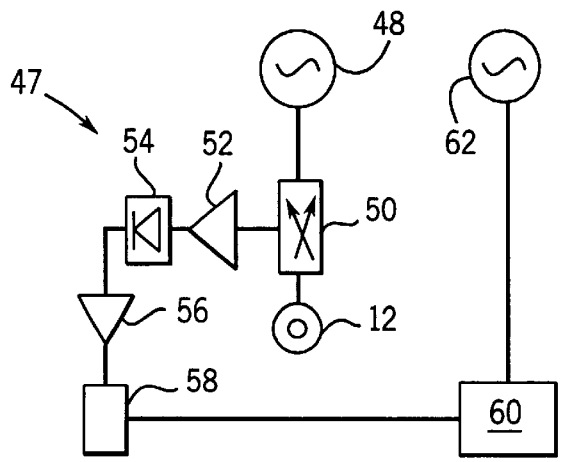
FIG. 5 is a schematic diagram of the density sensor.

Referring to FIG. 5, a schematic drawing of the density sensor electronics 47 is illustrated. A radiation source 48 injects radiation into a coupler 50, which passes it on to the sensor 12. Radio or microwave frequency is preferred, but any suitable frequency may be used. In a preferred embodiment where the density of a cigarette rod is measured, the microwave frequency is at approximately 2 GHz. The portion of the radiation reflected from the sensor 12 is passed by the coupler 50 to a first amplifier 52. The amplified signal is converted to DC voltage by a detector 54 and the converted signal is amplified by a second amplifier 56. The output of the second amplifier 56 is digitized by an analog-to-digital converter (ADC) 58 and the digitized signal is passed to a microprocessor 60.

A typical cigarette manufacturing machine includes a shaft whose position indicates the stage of processing of the cigarette under consideration. A shaft encoder 62 of this shaft passes a signal to the microprocessor 60. A typical shaft may have one full revolution for every four cigarettes. The density of the tobacco typically needs to be measured in thirty-two different locations. The shaft encoder 62 therefore indicates, one hundred and twenty-eight times per revolution, that a location of interest is present within the sensor. The microprocessor 60 notes this fact and strobes the ADC 58 to digitize the signal at that moment. A density sensor 12 useable with the present invention can be found in U.S. Pat. No. 5,698,986 issued to Mays et al., which is hereby incorporated by reference. The Mays et al. patent is assigned to the Allen-Bradley Company, Inc., the assignee of the present application, and can be modified as disclosed herein for use in the present invention.

Figure 2:
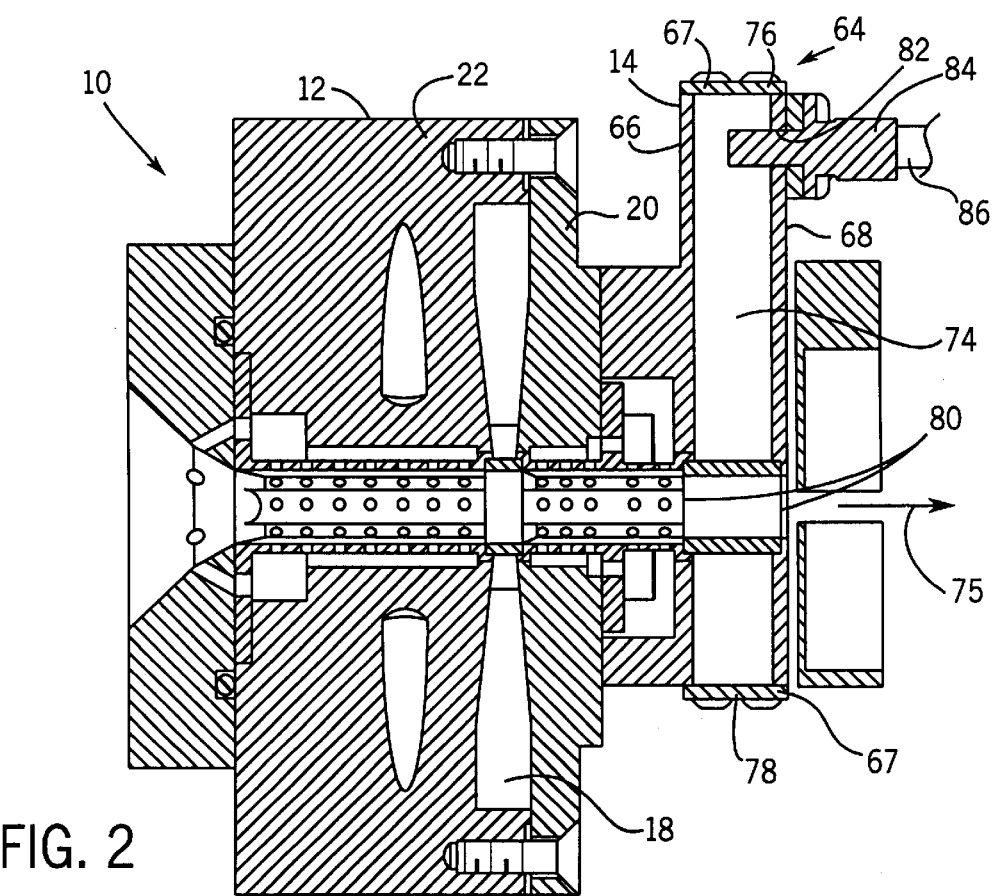
FIG. 2 is a section view taken along line 2—2 of FIG. 1.

Referring to FIGS. 1 and 2, the free water sensor 14 includes a waveguide 64 having front and back sides 66, 68 disposed opposite each other. Opposing sidewalls 70, 72 are connected perpendicular to the front and back sides 66, 68 at edges thereof to define a chamber 74 therewithin. The waveguide 64 is formed of metal, such as aluminum or copper with the chamber being sized and configured for propagating a microwave signal therethrough. In the preferred embodiment shown, the waveguide has a generally rectangular cross section, as illustrated in the drawings, and has dimensions of approximately 3.0 inches long, 1.0 inch wide, 0.5 inches between the front and back sides 66, 68. The wall thickness of the waveguide for the respective sides being approximately 0.05 inch. However, it should be understood that other dimensions for the sensor 14 could be used in other applications or embodiments.

The waveguide 64 has first and seconds ends 76, 78 perpendicular to the front and back sides 66, 68 forming a short within the chamber 74. In the preferred embodiment, the ends 76, 78 each include a side plate 67 mounted to the sides 66, 68 and sidewalls 70, 72 to enclose the chamber 74 at opposite ends thereof The front and back sides 66,68 each having a second aperture 80 extending substantially perpendicular therethrough between the first and second ends 76, 78 and coaxial with one another. The apertures 80 being sized for receiving a substance therethrough where it would enter through one aperture 80 and exit though the other aperture 80, as represented by arrow 75 in FIG. 2. In the preferred embodiment shown, the apertures 80 are circular and are sized to receive a cigarette rod, as later described.

Figure 6:
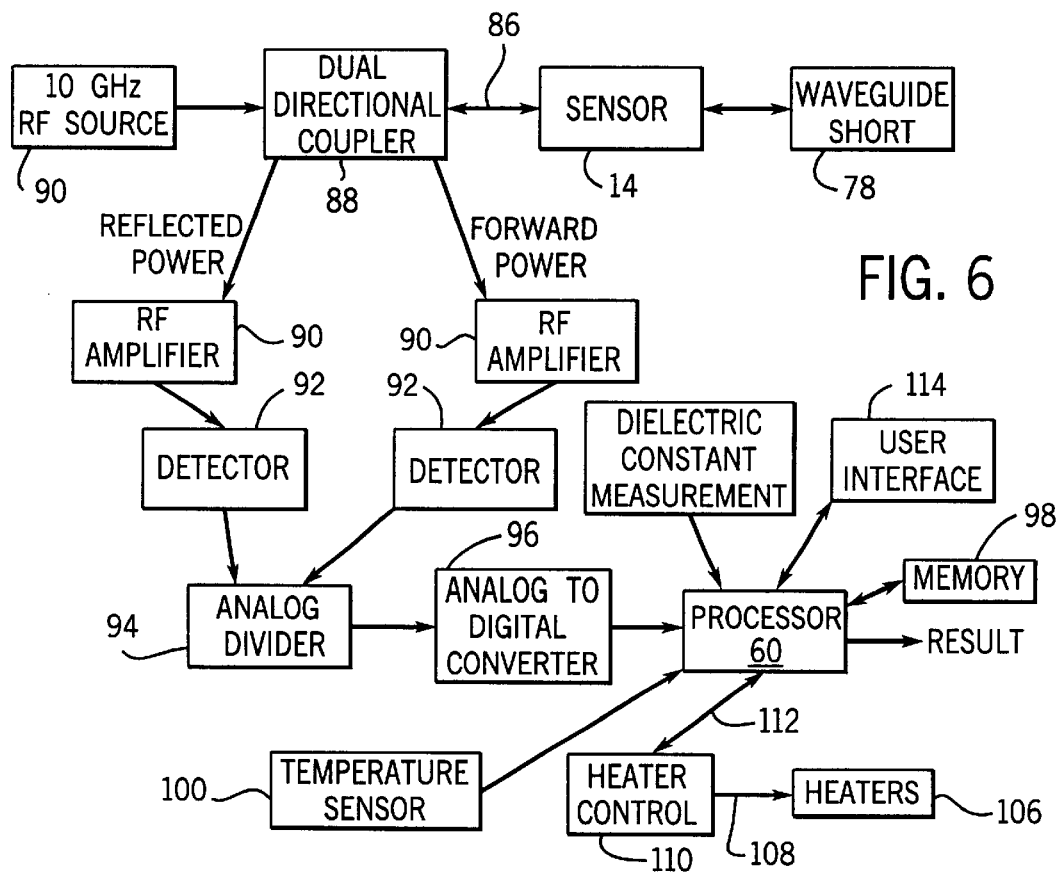
FIG. 6 is a schematic diagram of the of the present invention.

The waveguide 64 has a connector aperture 82 in communication with the chamber 72, as best illustrated in FIG. 2. The connector aperture 82 receives a coupler 84, such as a coax coupler adapted to receive an end of coax cable 86. Referring to FIG. 6, the cable 86 connects to a dual directional coupler 88 of conventional construction which is connected to a conventional radio or microwave signal source 90 to transmit a radio or microwave signal into and out of the connector aperture 82 through the coupler 84. The microwave signal has a frequency in the range of approximately 10–25 gigahertz (GHz). In a preferred embodiment, the microwave signal is approximately 10 GHz. The coupler 84 is positioned adjacent to the first end 76 at a distance to prevent any undesired feedback. The microwave signal will travel through the chamber 74 and through a substance to be measured which extends transversely across the chamber 74, which causes some of the signal to be absorbed by the substance. The signal will be reflected back from the second short or end 78. The dual directional coupler 88, operating at 30 dB in a preferred embodiment, samples both the forward power transmitted to the sensor 14 and reflected from the sensor 14, as described above. The power samples or voltage signals are amplified, if necessary, by RF amplifiers 90 and are fed to detectors 92 connected with the amplifiers 90. Output voltages from the detectors 92 are amplified by operational amplifiers of conventional design and fed to an analog divider 94.

The ratio presented to the analog divider 94 represents the attenuation between the forward power or signal and the reflected power or signal which was measured by the dual directional coupler 88. The output of the analog divider 94 is fed to an analog-to-digital converter 96 connected thereto which digitizes the output into a digital output. The digital output signal is then passed to the processor 60, which is connected with the converter 96.

The microprocessor 60 is also configured for receiving the dielectric constant or coefficient measurement as previously discussed and is thereby able to calculate a weight of the substance from the received digital output, dielectric constant measurement, and by having information of the related properties of the substance's constituents, which may be stored in memory 98 accessible by the processor 60.

The general form of the algorithm for calculating the cigarette weight in the preferred embodiment including the effects of temperature, discussed below, and free water is as follows:

$$W = m[(\Delta_{2GHz} - f\{t\}) - K_{FW} * \Delta_{10GHz}] + b$$

Where:
W is cigarette weight;
m is a cigarette weight scale factor;
$\Delta_{2GHz}$ is the sensor head resonant frequency shift at 2 GHz;
f{t} is the frequency shift correction for temperature t;
$\Delta_{10GHz}$ is the measured attenuation at 10 GHz;
$K_{FW}$ is a free water scale factor; and
b is a cigarette weight offset value It should be noted that the values of m and b are supplied by the user for particular application, and are applied by the cigarette weight system processor 60 in the aforementioned calculations.

Figure 3:
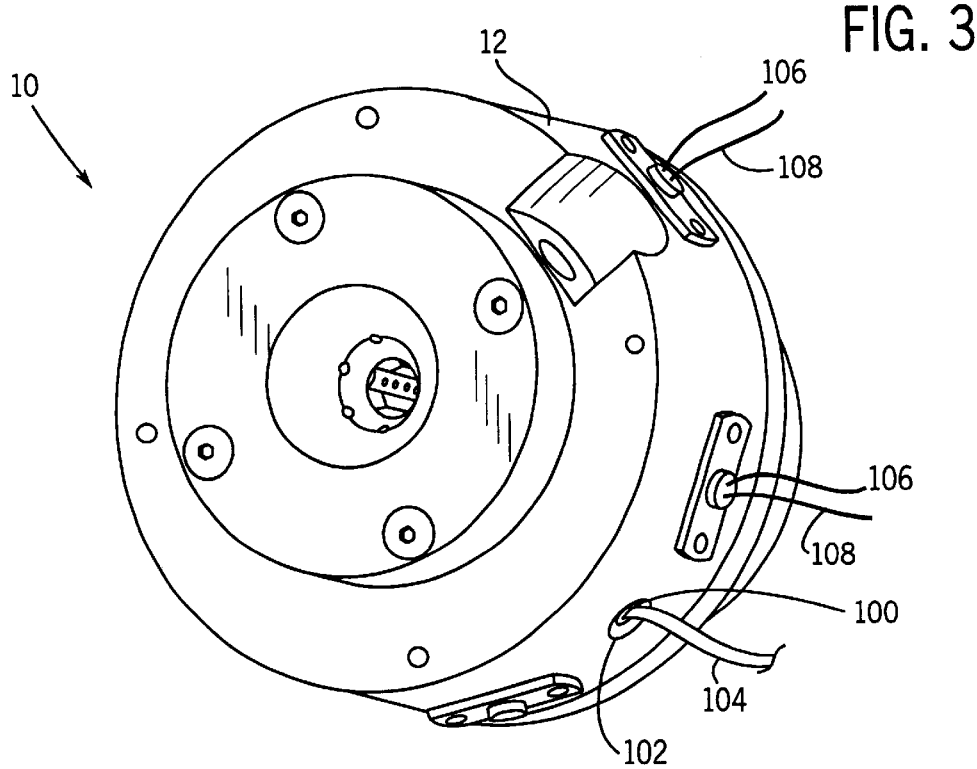
FIG. 3 is a perspective view illustrating the sensor heaters.

To provide a better measurement of the tobacco density in the cigarette rod being measured, a correction factor can be applied to account for changes in the temperature of the sensor head (resonant cavity) of sensor 12. Referring to FIG. 6, a temperature sensor 100 is connected to the processor 60 to provide signals representing the temperature of the sensor 12 for use in the above calculations. Referring to FIG. 3, sensor 12 has an aperture 102 for receiving the temperature sensor 100 which is mounted therewithin. Wire 104 is connected between the sensor 100 and the processor 60 to transmit temperature signals.

In another embodiment, to reduce the effect of any residual error due to temperature variations, heaters 106 can be added to the sensor 12 to maintain it's temperature above the expected ambient, as illustrated in FIG. 3. This will isolate the sensor 12 from changes in the environment such as will occur when the cigarette making machine is stopped, allowed to cool, and restarted. Referring to FIGS. 3 and 6, the heaters 106 are connected across lines 108 to a heater control circuit 110 of known design which will control the heaters 106 to maintain a desired temperature. The results of the heater settings may be supplied to the processor 60 across line 112 which connects the heater control circuit 110 with the processor 60. Alternatively, a user interface 114 connected with the processor 60 may be utilized to set the control circuit 110 to a desired temperature.

Figure 7:
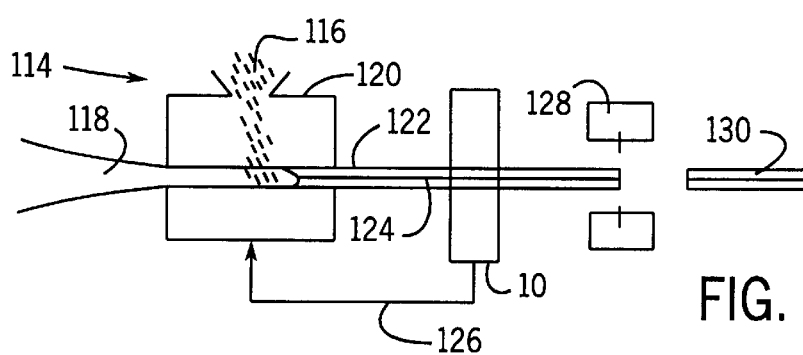
FIG. 7 is a schematic diagram of a cigarette manufacturing apparatus including the apparatus of the present invention and the machinery associated with it.

Referring to FIG. 7, a cigarette manufacturing system 114 is disclosed. Air borne grains of tobacco 116 and a sheet of cigarette paper 118 are applied to a cigarette manufacturing machine 120. The machine 120 seals the grains 116 into a continuous tobacco rod 122, formed by forming the paper 118 into tube, inserting the grains 116, and sealing the edges of the paper 118 into a seal 124. The tobacco rod 122 passes through the density monitor 10 including its associated electronics of FIGS. 5 and 6. In particular, it should be noted that the sensors 12, 14 are adjacent one another with the apertures 34, 36, 80 all being coaxial along line 123, with the rod 122 extending therethrough, as illustrated in FIG. 4, for continuous movement during the manufacturing process. The close proximity of the adjacent sensors 12, 14 allows adjacent segments or portions of the rod 122 or substance to be measured.

Referring back to FIG. 7, a control signal from the processor 60 is fed back in a feedback loop 126 to the machine 120 to control the forming of the rod 122 in response to the control signal. More particles of grain 116 are added to the rod 122 when the control signal indicates that the desired weight of a comparable portion of a previous package is below a lower control limit. Fewer particles of grain 116 are added to the rod 122 when the control signal indicates that the desired measurement of a comparable portion of a previous package is above an upper control limit. When the rod 122 emerges from the sensor 10, a cutter 128 cuts it into individual cigarettes 130.

While the preferred embodiment of the present invention relates to a method and apparatus for use in the cigarette manufacturing process, it should be appreciated that the present invention could be used in other processes seeking similar results or measurements.

Although the invention has been described by reference to some embodiments it is not intended that the novel device be limited thereby, but that modifications thereof are intended to be included as falling within the broad scope and spirit of the foregoing disclosure, the following claims and the appended drawings.

What is claimed is:

1. Method of measuring the weight of a substance traveling continuously in a production process, the method comprising the steps of:

providing a first sensor having a first aperture extending therethrough, the first sensor defining a resonant cavity and having circuitry operatively connected therewith, the circuitry being operatively connected to a processor for measuring a dielectric constant measurement corresponding to the density of the substance passing continuously through the first aperture of the first sensor and through said cavity;

providing a second sensor having a waveguide defining a chamber therewithin, said chamber being sized and configured for propagating a microwave signal therethrough, said waveguide having an end forming a short within said chamber, said waveguide having a second aperture extending substantially perpendicular through said waveguide and generally parallel with the end;

directing the substance continuously through said second aperture;

directing a microwave signal having a frequency in the range of 10–25 GHz through said chamber;

detecting the microwave signal directed into said chamber and detecting the microwave signal reflected back from said short;

converting the detected microwave signals into a ratio and converting the ratio into a digitized signal for receipt by the processor; and determining within the processor a weight of the substance using the dielectric constant measurement and compensating the weight with said digitized signal of the ratio corresponding to the amount of free water contained within the substance.

2. The method of claim 1, further comprising the step of positioning the first sensor and second sensor immediately adjacent one another for simultaneously measuring adjacent segments of the substance.

3. The method of claim 2, further comprising the step of forming a rod by forming a sheet into a tube and inserting the substance into the tube as it is formed, and continuously directing the rod through the first and second apertures.

4. The method of claim 2, wherein the first aperture is disposed coaxial with the second aperture.

5. The method of claim 1, further comprising the steps of determining the temperature of the first sensor, and determining the weight of the substance by compensating the weight based on the temperature of the first sensor.

6. The method of claim 1, further comprising the step of providing heaters within the first sensor and heating the first sensor to maintain a predetermined temperature of the first sensor.

7. Apparatus for measuring the weight of a substance having compensation for amounts of free water contained within the substance, the apparatus comprising:

first sensor means for measuring a dielectric constant of the substance, said first sensor means having a resonant cavity and circuitry operatively connected therewith, the first sensor means having a first aperture extending therethrough, the circuitry being operatively connected to a processor for providing a dielectric constant measurement corresponding to the density of the substance passing through the first aperture and through said cavity;

second sensor means for measuring free water contained within the substance, said second sensor means having a waveguide defining a chamber therewithin, said chamber being sized and configured for propagating a microwave signal therethrough, said waveguide having first and second ends forming a short on each of said first and second ends within said chamber, said waveguide having a second aperture extending substantially perpendicular through said waveguide between said first and second ends, said second aperture being sized for receiving a substance therethrough in communication with said chamber, said second sensor means having means for generating a microwave signal through said chamber and receiving back the microwave signal reflected from said short disposed at said second end and converting said signals into a ratio provided as a digital signal transmitted to the processor which is operatively connected therewith; and the processor having means for receiving said dielectric constant measurement from said first sensor means and said ratio from said second sensor means and determining the weight of the substance by applying said dielectric constant measurement and ratio.

8. The apparatus of claim 7, wherein said waveguide is sized and configured to propagate a 10 GHz microwave signal.

9. The apparatus of claim 7, wherein said first sensor means includes means for generating a microwave signal at a first predetermined frequency for propagating through said resonant cavity, and generating the microwave signal of said second sensor means at a second predetermined frequency different from said first predetermined frequency.

10. The apparatus of claim 9, wherein the first predetermined frequency is approximately 2 GHz and the second predetermined frequency is in the range of 10–25 GHz.

11. The apparatus of claim 10, wherein the second predetermined frequency is approximately 10 GHz.

12. The apparatus of claim 9, wherein said waveguide has a generally rectangular cross section.

13. The apparatus of claim 9, wherein said first and second apertures are circular and sized for receiving a cigarette rod.

14. The apparatus of claim 9, wherein said first and second apertures are generally coaxial.

15. The apparatus of claim 7, further comprising means for determining the temperature of the first sensor means, and means for determining the weight of the substance by compensating the weight based on the temperature of the first sensor means.

16. The method of claim 15, further comprising heaters connected to the first sensor means for heating the first sensor means to maintain a predetermined temperature.

17. A package of particles manufactured by a process comprising the steps of:

forming a rod by forming a sheet into a tube and inserting particles into the tube as it is formed;

providing a first sensor having a first aperture extending therethrough, the first sensor defining a resonant cavity and having circuitry operatively connected therewith, the circuitry being operatively connected to a processor for measuring a dielectric constant corresponding to the density of the rod passing continuously through the first aperture of the first sensor and through said cavity;

providing a second sensor having a waveguide defining a chamber therewithin, said chamber being sized and configured for propagating a microwave signal therethrough, said waveguide having an end forming a short within said chamber, said waveguide having a second aperture extending substantially perpendicular through said waveguide and generally parallel to the end;

directing the rod continuously through said second aperture;

directing a microwave signal having a frequency in the range of 10–25 GHz through said chamber;

detecting the microwave signal directed into said chamber and detecting the microwave signal reflected back from said short;

converting the detected microwave signals into a ratio and converting the ratio into a digitized signal for receipt by the processor;

determining within the processor a weight of a portion of the rod using the dielectric constant measurement and compensating the weight with said digitized signal of the ratio corresponding to the amount of free water contained within the portion of the rod, the processor generating a control signal corresponding to the compensated weight of the portion of the rod;

controlling the forming of the rod in response to the control signal from the processor by adding more particles to the rod when the control signal indicates that the desired weight of a comparable portion of a previous package is below a lower control limit, and adding fewer particles to the rod when the control signal indicates that the desired measurement of a comparable portion of a previous package is above an upper control limit; and cutting an individual package from the rod.

18. The package of claim 17, further comprising the step of positioning the first sensor and second sensor immediately adjacent one another for simultaneously measuring adjacent segments of the substance.

19. The package of claim 18, wherein the first aperture is disposed coaxial with the second aperture.

20. The package of claim 18, wherein the package comprises a cigarette, the particles comprise grains of tobacco, and the sheet comprises cigarette paper.

21. Apparatus for measuring the weight of a continuously moving substance having compensation for amounts of free water contained within the substance, the apparatus comprising:

a first sensor for measuring a dielectric constant of the substance, said first sensor having a resonant cavity and circuitry operatively connected therewith, the first sensor having a first aperture extending therethrough, the circuitry being operatively connected to a processor for providing a dielectric constant measurement corresponding to the density of the substance passing through the first aperture and through said cavity;

a second sensor for measuring free water contained within the substance, said second sensor defining a chamber therewithin, said chamber being sized and configured for propagating a microwave signal therethrough, said second sensor having a second aperture extending substantially perpendicular through said second sensor, said second aperture being sized for receiving a substance therethrough in communication with said chamber, said second sensor having means for generating a microwave signal through said chamber and receiving back the reflected microwave signal and converting said signals into a ratio provided as a digital signal transmitted to the processor which is operatively connected therewith; and the processor receiving said dielectric constant measurement from said first sensor and said ratio from said second sensor and determining the weight of the substance by applying said dielectric constant measurement and ratio.

* * * * *